(12) United States Patent  (10) Patent No.: US 7,651,491 B2
Nobis et al.  (45) Date of Patent: Jan. 26, 2010

(54) METHOD FOR PERFORMING AN ENDOSCOPIC MUCOSAL RESECTION

(75) Inventors: Rudolph H. Nobis, Mason, OH (US); Ifung Lu, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 446 days.

(21) Appl. No.: 11/414,627

(22) Filed: Apr. 28, 2006

(65) Prior Publication Data

US 2007/0255268 A1  Nov. 1, 2007

(51) Int. Cl.
A61B 18/14 (2006.01)

(52) U.S. Cl. .............................. 606/32; 606/45; 606/47

(58) Field of Classification Search .......... 606/1.32–52, 606/205–208
See application file for complete search history.

(56) References Cited

U.S. PATENT DOCUMENTS

| | | | |
|---|---|---|---|
| 3,910,279 A | 10/1975 | Okada et al. | |
| 5,282,826 A * | 2/1994 | Quadri | 606/207 |
| 5,411,519 A | 5/1995 | Tovey et al. | |
| 5,511,564 A | 4/1996 | Wilk | |
| 5,772,627 A | 6/1998 | Acosta et al. | |
| 5,797,959 A | 8/1998 | Castro et al. | |
| 5,961,526 A | 10/1999 | Chu et al. | |
| 6,022,362 A | 2/2000 | Lee et al. | |
| 6,096,037 A | 8/2000 | Mulier et al. | |
| 6,191,365 B1 | 2/2001 | Avellanet | |
| 6,319,260 B1 | 11/2001 | Yamamoto | |
| 6,331,166 B1 | 12/2001 | Burbank et al. | |
| 2003/0191465 A1 | 10/2003 | Yahagi et al. | |
| 2003/0236549 A1 | 12/2003 | Bonadio et al. | |
| 2004/0167514 A1 | 8/2004 | Okada | |
| 2005/0049454 A1 | 3/2005 | Ouchi | |

(Continued)

FOREIGN PATENT DOCUMENTS

EP  1479351  11/2004

(Continued)

OTHER PUBLICATIONS

"Technology Status Evaluation Report—Endoscopic Mucosal Resection," ASGE Gastrointestinal Endoscopy, vol. 52, No. 6, pp. 860-863 (2000).

*Primary Examiner*—Michael Peffley
*Assistant Examiner*—Ronald J Hupczey, Jr.
(74) *Attorney, Agent, or Firm*—Gerry S. Gressel

(57) ABSTRACT

A method for resecting tissue from an organ of a patient, the organ being comprised of at least a first layer, a second layer and a third layer, the method including the steps of providing an EMR device with access to the organ, the EMR device including at least one deployable cutting element disposed on at least one moveable arm, identifying a target tissue area for resection, forming an incision through the first and second layers without penetrating the third layer, positioning the EMR device through the incision such that the device is positioned between the first third layers, advancing the moveable arm between the first and third layers, deploying the cutting element such that the cutting element is advanced in the direction of the first layer and away from the third layer and, while the EMR device is positioned between the first and third layers, cutting through the first layer.

15 Claims, 21 Drawing Sheets

U.S. PATENT DOCUMENTS

| | | |
|---|---|---|
| 2005/0072280 A1 | 4/2005 | Ono et al. |
| 2005/0149099 A1 | 7/2005 | Yamano et al. |
| 2005/0165437 A1* | 7/2005 | Takimoto .................... 606/190 |
| 2005/0171531 A1 | 8/2005 | Eliachar et al. |
| 2005/0215996 A1 | 9/2005 | Ouchi |
| 2005/0251134 A1 | 11/2005 | Woloszko et al. |
| 2008/0015574 A1* | 1/2008 | Karpiel ....................... 606/46 |

FOREIGN PATENT DOCUMENTS

| | | |
|---|---|---|
| WO | WO 2005/079682 | 9/2005 |

* cited by examiner

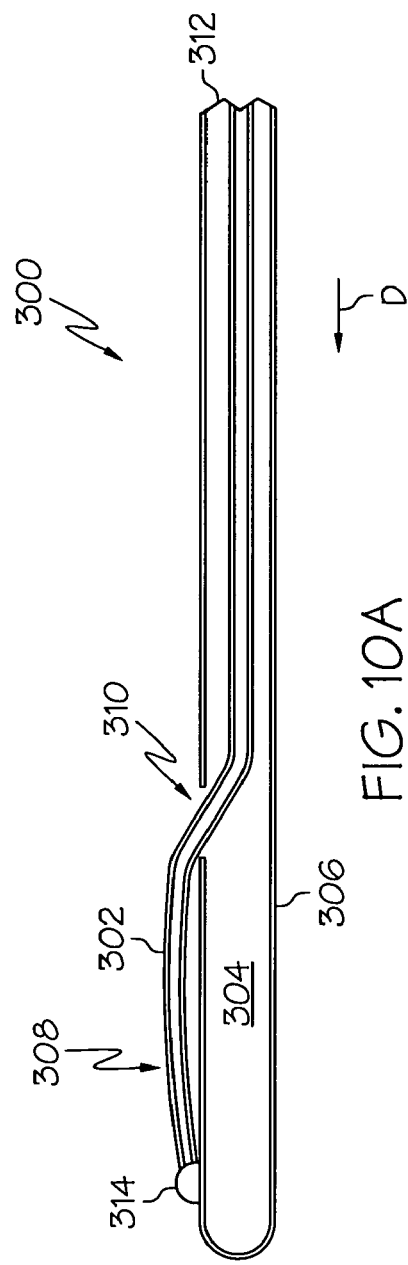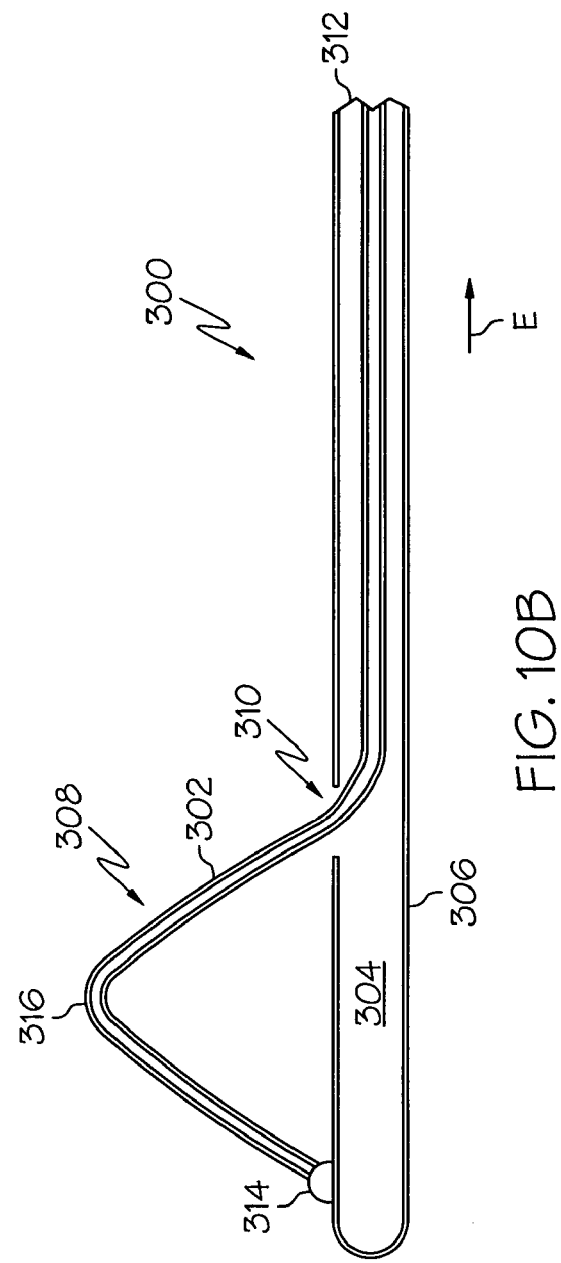

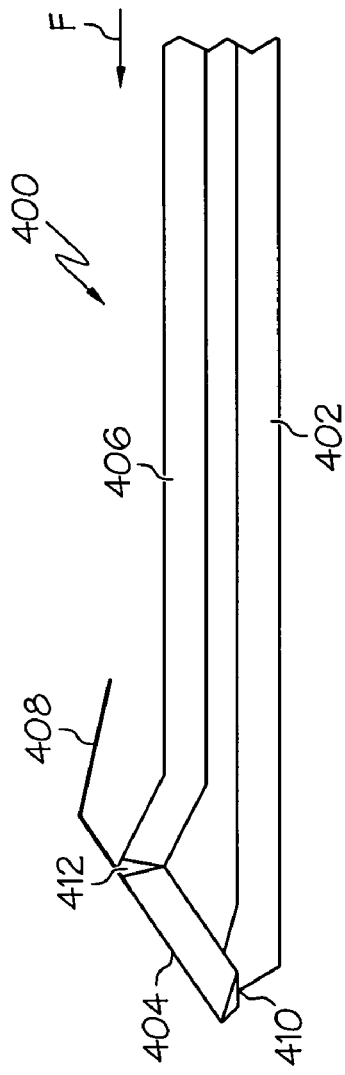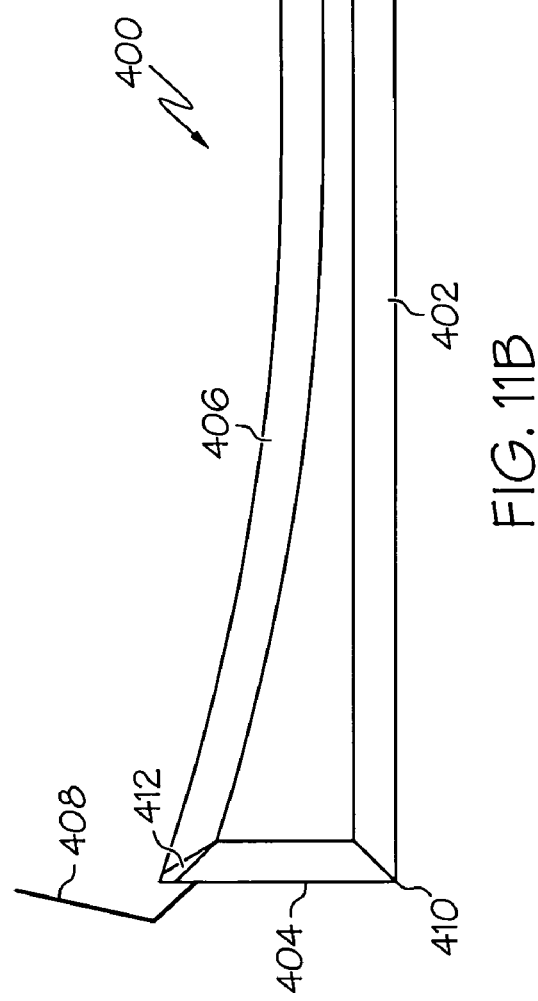
FIG. 11A
FIG. 11B

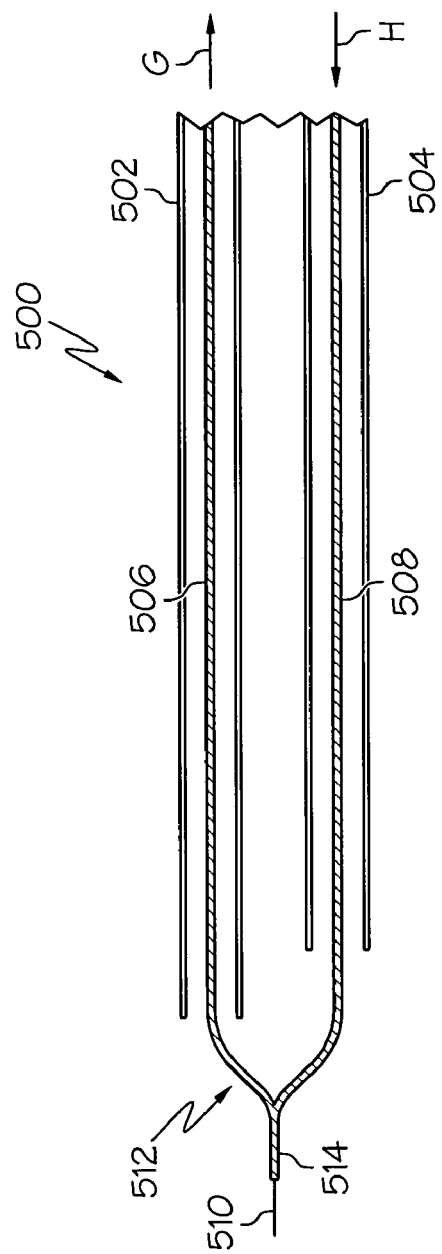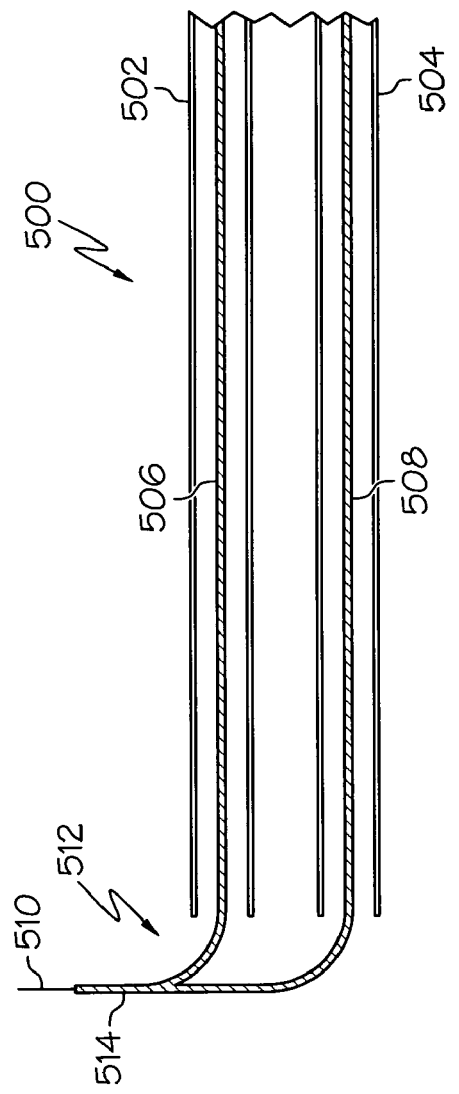

METHOD FOR PERFORMING AN ENDOSCOPIC MUCOSAL RESECTION

FIELD OF THE INVENTION

The present application relates to medical devices and methods and, more particularly, to medical devices and methods for performing resection procedures within the gastrointestinal and esophageal passages of the human body.

BACKGROUND OF THE INVENTION

Gastric cancers in the human body often stem from precursor lesions and polyps that develop into superficial tumors or other growths. Such lesions and growths typically begin in the mucosal layer of the gastrointestinal tract (e.g., the mucosa of the colon) and, as the cancer develops, may spread to the submucosal layer and beyond. Therefore, many physicians agree that successful cancer treatment and prevention typically requires the identification and removal of suspect tissue from the gastrointestinal tract.

Accordingly, physicians may collect samples of tissue from the gastrointestinal tract (e.g., samples of the mucosa) and test the sample tissue for the presence of cancerous cells. The tissue sampling may be purely prophylactic or may be conducted in response to symptoms indicative of cancer. When cancerous lesions or the like are detected, curative treatments often require complete resection of the suspect tissue.

Various techniques have been developed for removing tissue from the walls of the gastrointestinal tract. Such techniques commonly employ an endoscope that enters the body through a natural orifice (e.g., the anus) and, therefore, often are referred to as endoscopic mucosal resection ("EMR") techniques.

Prior art EMR techniques typically include a "lift-and-cut" procedure, wherein a snare and forceps is used to grasp and lift the lesion while the physician cuts around the lesion. The cut typically is made through the mucosa and submucosa, taking particular caution not to penetrate the muscularis. However, such techniques have presented several disadvantages, including the difficulty associated with removing the entire suspect region and the risk of penetrating the muscularis during cutting.

Accordingly, there is a need for an improved apparatus and method for performing resection procedures within the gastrointestinal and esophageal passages of the human body.

SUMMARY OF THE INVENTION

In one aspect, a method for resecting tissue from an organ of a patient is provided and includes the steps of providing an EMR device with access to the organ, the EMR device including at least one deployable cutting element disposed on at least one moveable arm, identifying a target tissue area for resection, forming an incision through the first and second layers without penetrating the third layer, positioning the EMR device through the incision such that the device is positioned between the first third layers, advancing the moveable arm between the first and third layers, deploying the cutting element such that the cutting element is advanced in the direction of the first layer and away from the third layer and, while the EMR device is positioned between the first and third layers, cutting through the first layer.

In another aspect, a method for resecting tissue from an organ of a patient is provided, the organ including at least a first layer and a second layer, the method comprising the steps of positioning an EMR device in the first layer, the EMR device including at least one deployable cutting element disposed on at least one moveable arm, advancing the moveable arm through the first layer, deploying the cutting element such that the cutting element is advanced through the first layer in a direction generally away from the second layer and, while the EMR device is positioned in the first layer, cutting through the first layer.

Other aspects of the disclosed method for performing an endoscopic mucosal resection will become apparent from the following description, the accompanying drawings and the appended claims.

BRIEF DESCRIPTION OF THE FIGURES

FIG. 10A is an elevational view, partially in section, of a first alternative aspect of a cutting element;

FIG. 10B is an elevational view, partially in section, of the cutting element of FIG. 10A in a deployed position;

FIG. 11A is an elevational view of a second alternative aspect of a cutting element;

FIG. 11B is an elevational view of the cutting element of FIG. 11A in a deployed position;

FIG. 12A is an elevational view, partially in section, of a third alternative aspect of a cutting element;

FIG. 12B is an elevational view, partially in section, of the cutting element of FIG. 12A in a deployed position;

DETAILED DESCRIPTION OF THE INVENTION

Figure 1:
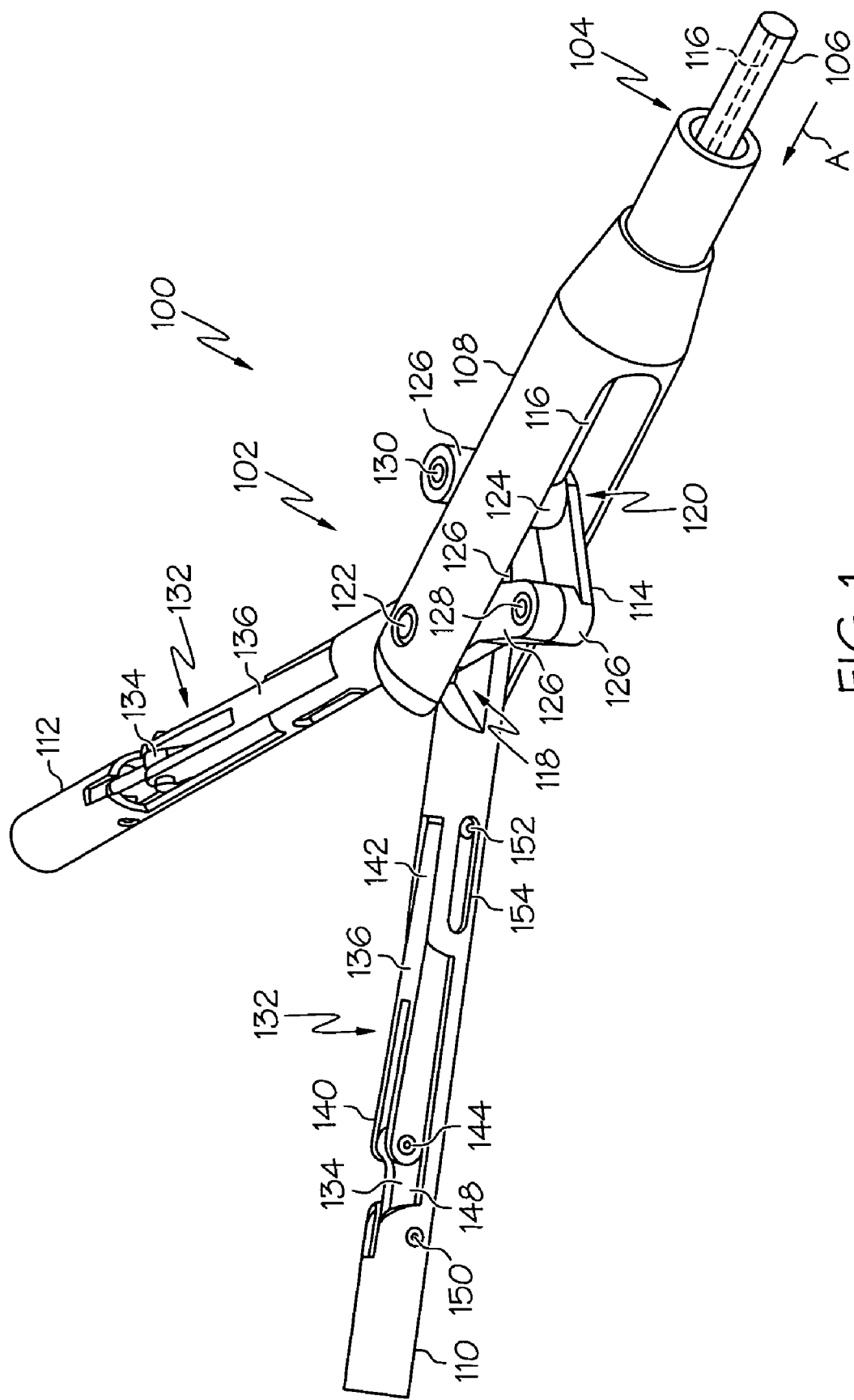
FIG. 1 is a perspective view of one aspect of the disclosed apparatus for performing an EMR procedure.

Referring to FIGS. 1-4, a first aspect of an improved EMR device, generally designated 100, may include a dissection/actuation assembly 102 disposed on the distal end 104 of an elongated shaft 106. The assembly 102 and shaft 106 may be sized and shaped to be received through a natural orifice of the human body (not shown). The shaft 106 may be flexible and may have a length sufficient to navigate the human gastrointestinal tract during an endoscopic procedure.

The assembly 102 may include a head 108, a first moveable arm 110, a second moveable arm 112, a linkage assembly 114 and an actuation link or cable 116. The linkage assembly 114 may be comprised of four pivotally connected links 126 and may be disposed within the head 108. The actuation cable 116 may extend through the elongated shaft 106 such that it is accessible by a user.

The linkage assembly 114 may include a distal end 118 and a proximal end 120, wherein the distal end 118 may be connected to the first and second arms 110, 112 at a first pivot point 122 and the proximal end 120 may be connected to the actuation cable 116 at a second pivot point 124. Additionally, the links 126 of the linkage assembly 114 may be connected at third and fourth pivot points 128, 130.

Figure 2:
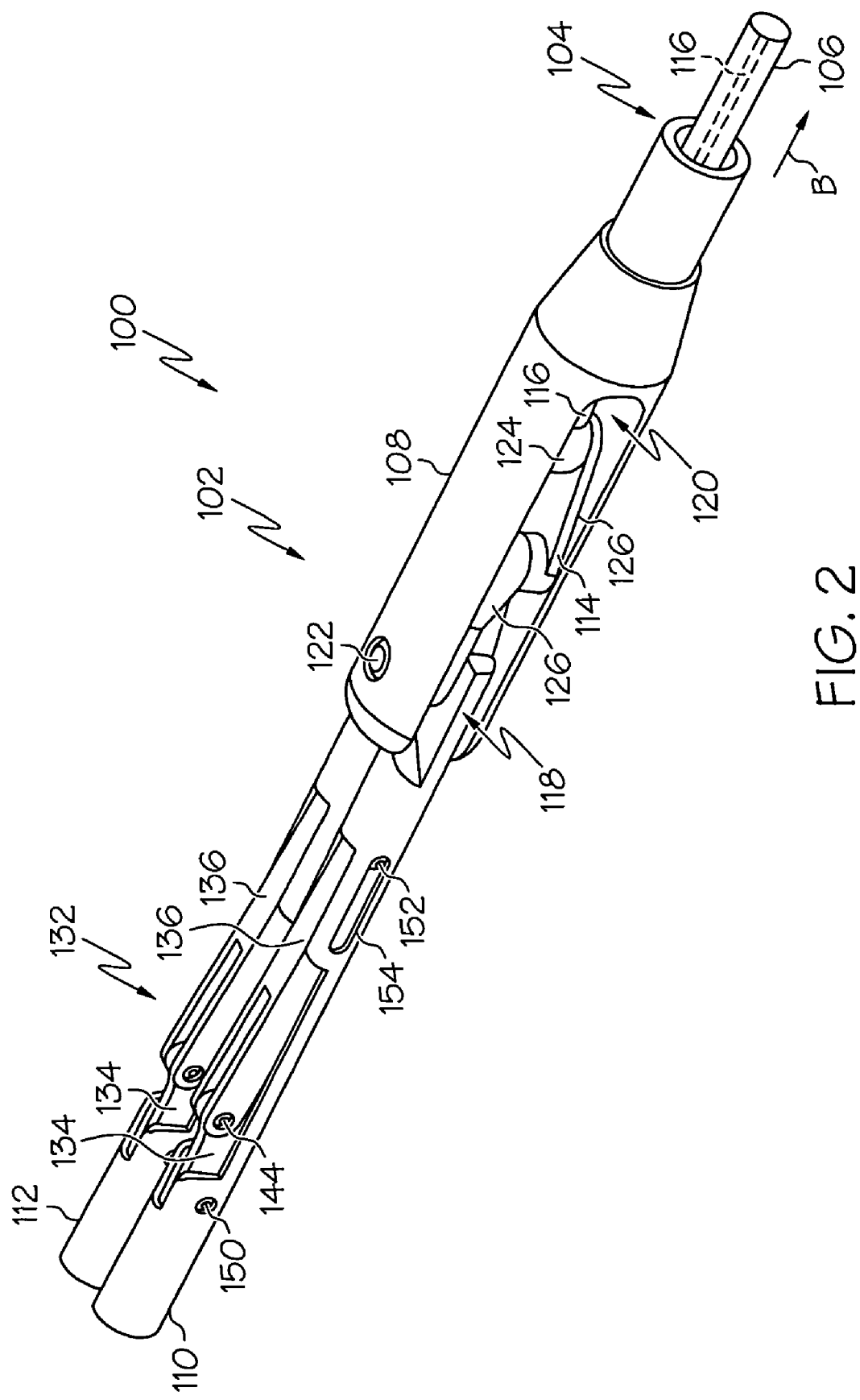
FIG. 2 is a perspective view of the apparatus of FIG. 1 in a second configuration.
Figure 3:
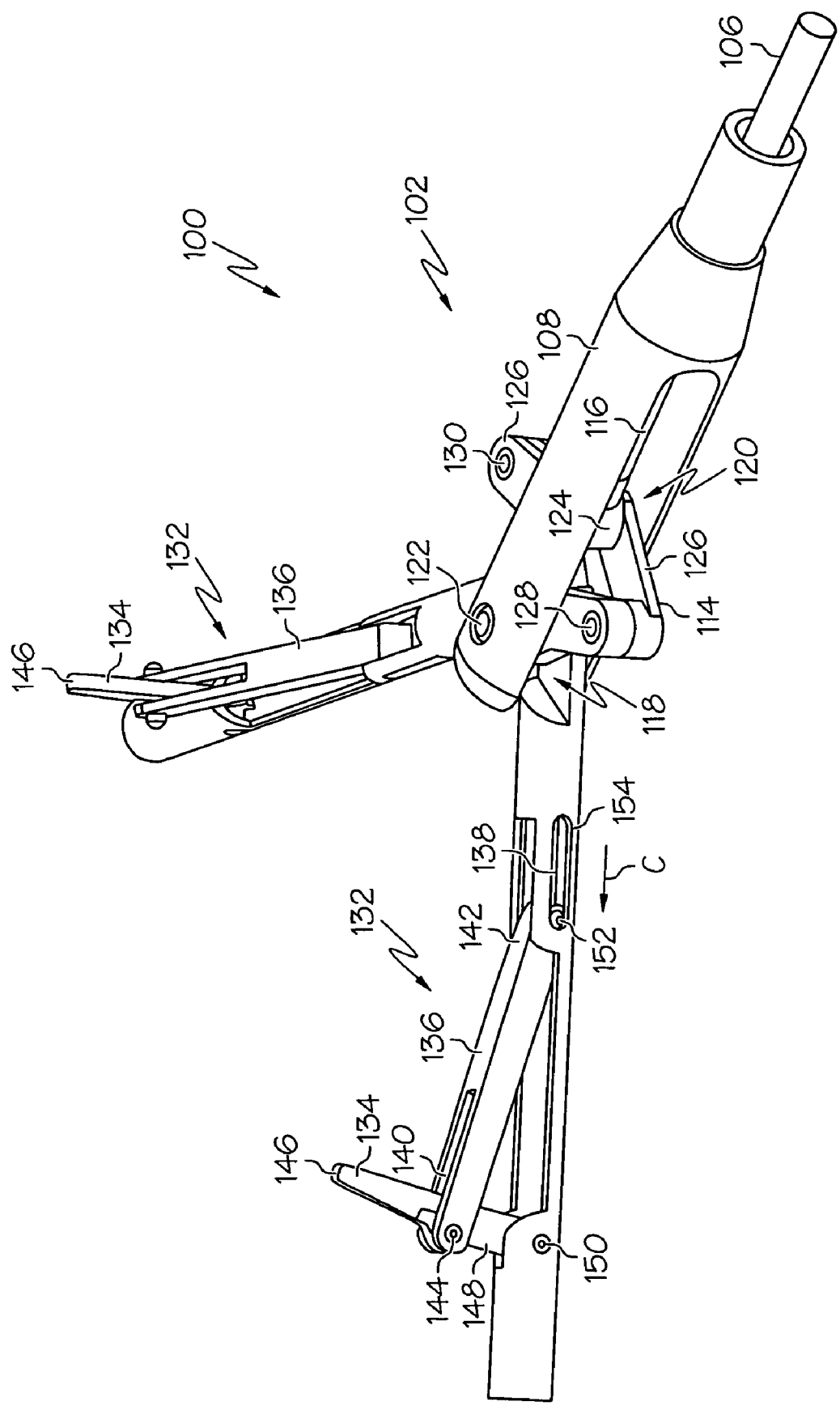
FIG. 3 is a perspective view of the apparatus of FIG. 1, wherein the cutting elements are in a deployed position.
Figure 4:
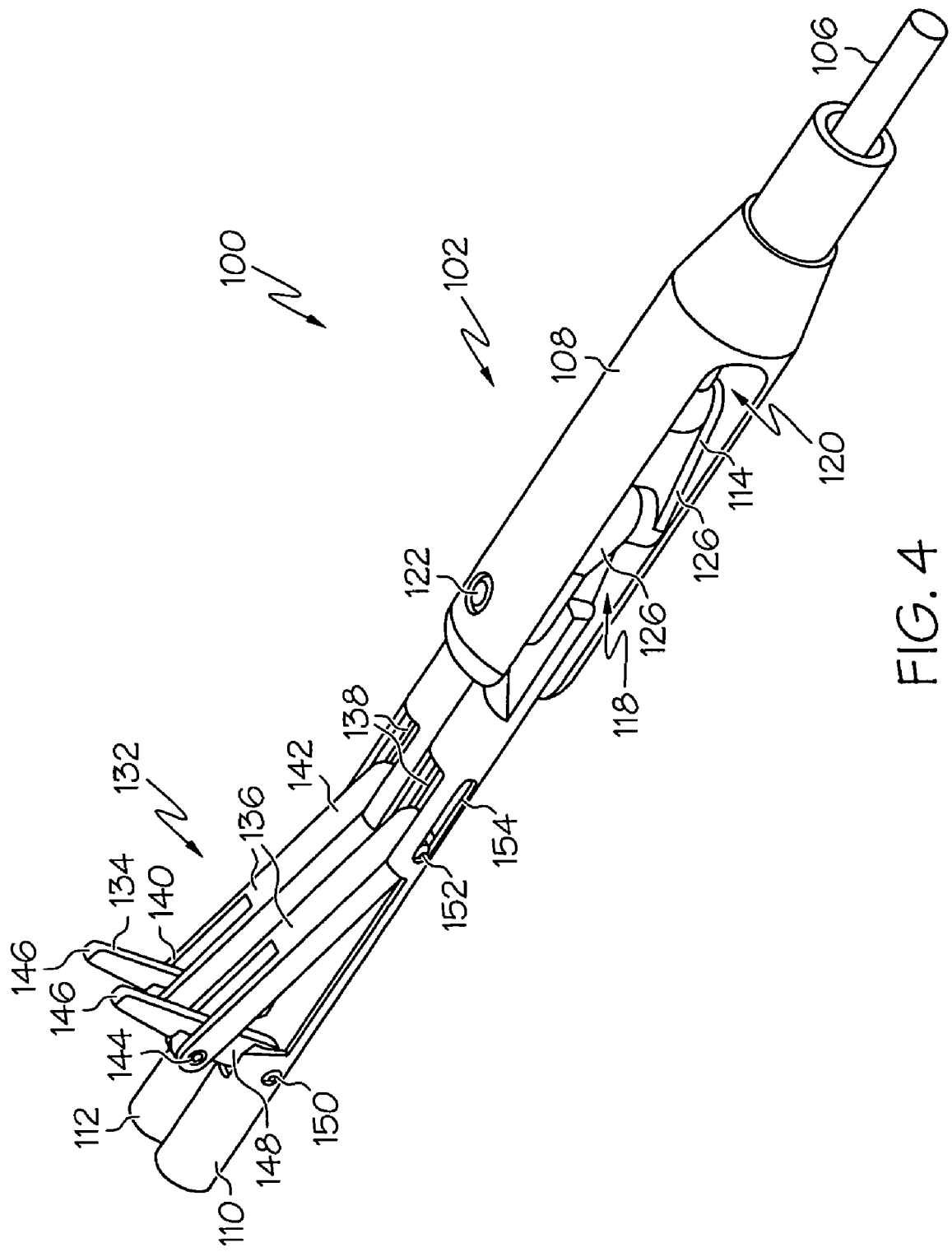
FIG. 4 is a perspective view of the apparatus of FIG. 3 in the second configuration.

Manipulation of the cable 116 in the direction shown by arrow A may achieve a compression of the linkage assembly 114 (i.e., the links 126 may extend radially with respect to the longitudinal axis of the device 100) and a corresponding pivot of the arms 110, 112 about pivot point 122 to an open configuration, as shown in FIGS. 1 and 3. Referring to FIGS. 2 and 4, manipulation of the cable 116 in the direction shown by arrow B may achieve expansion of the linkage assembly 114 (i.e., the links 126 may extend axially with respect to the longitudinal axis of the device 100) and a corresponding pivot of the arms 110, 112 about pivot point 122 to a closed configuration.

Accordingly, by manipulating the cable 116, a user can move the arms 110, 112 of the device 100 to an open position, a closed position or various positions therebetween in a scissor-like action. Thus, when the device 100 is positioned between layers of tissue, a user may bluntly dissect the tissue and separate the layers by urging the device through the tissue while using the scissor-like action described herein.

At this point, those skilled in the art will appreciate that the device 100 may be provided with various arms and/or linkage assemblies such that the arms move and/or separate relative to each other in various ways. For example, a linkage assembly may be provided such that the corresponding arms remain generally parallel while opening and closing.

Referring again to FIGS. 1-4, each arm 110, 112 may be provided with a deployable cutting element assembly 132 for deploying a cutting element 134. The cutting element 134 may be a monopolar knife, an electrocautery knife or other electrically activated cutting device. Alternatively, the cutting element 134 may be a mechanical cutting device such as a scalpel or the like.

The cutting element assembly 132 may advance the cutting element 134 from a first (i.e., not deployed) configuration, as shown in FIGS. 1 and 2, to a second (i.e., deployed) configuration, as shown in FIGS. 3 and 4. In one aspect, the cutting element 134 may be deployed in a generally radial direction with respect to the associated arm 110, 112. In another aspect, the cutting element 134 may be deployed in a direction that is generally perpendicular or at least partially transverse with respect to the plane of movement of the arms 110, 112.

In one aspect, in addition to the cutting element 134, the cutting element assembly 132 may include an actuation bar 136 connected to an actuation link or cable 138, wherein manipulation of the actuation cable 138 may facilitate deployment of the cutting element 134. The actuation cable 138 may extend through the shaft 106 such that it may be manipulated by a user at the proximal end of the shaft 106. In one aspect, the actuation cable 138 may be connected to a power source and may provide monopolar electrical energy to the cutting element 134.

The cutting element 134 may include a cutting tip 146 and a pivot end 148, wherein the pivot end 148 of the cutting element 134 is pivotally connected to the associated arm 110, 112 at a pivot point 150. The actuation bar 136 may include a distal end 140 and a proximal end 142, wherein the distal end 140 may be pivotally connected to the cutting element 134 at a pivot point 144. The proximal end 142 of the actuation bar 136 may be connected to the actuation cable 138 and may include a pin 152 slidably engaged with a camming track 154 in the associated arm 110, 112.

Accordingly, manipulation (e.g., pushing, pulling, twisting or the like) of the actuation cable 138 may urge the actuation bar 136 in the direction shown by arrow C, thereby urging the cutting element 134 to the deployed position. Furthermore, reversing the manipulation may retract the cutting element 134 into the associated arm 110, 112 of the device 100.

Referring to FIGS. 5-9, an alternative aspect of the improved EMR device, generally designated 200, may include a dissection/actuation assembly 202 disposed on the distal end 204 of an elongated shaft 206. The assembly 202 may be manipulated by user controls (not shown) disposed at the proximal end (not shown) of the shaft 206.

Figure 5:
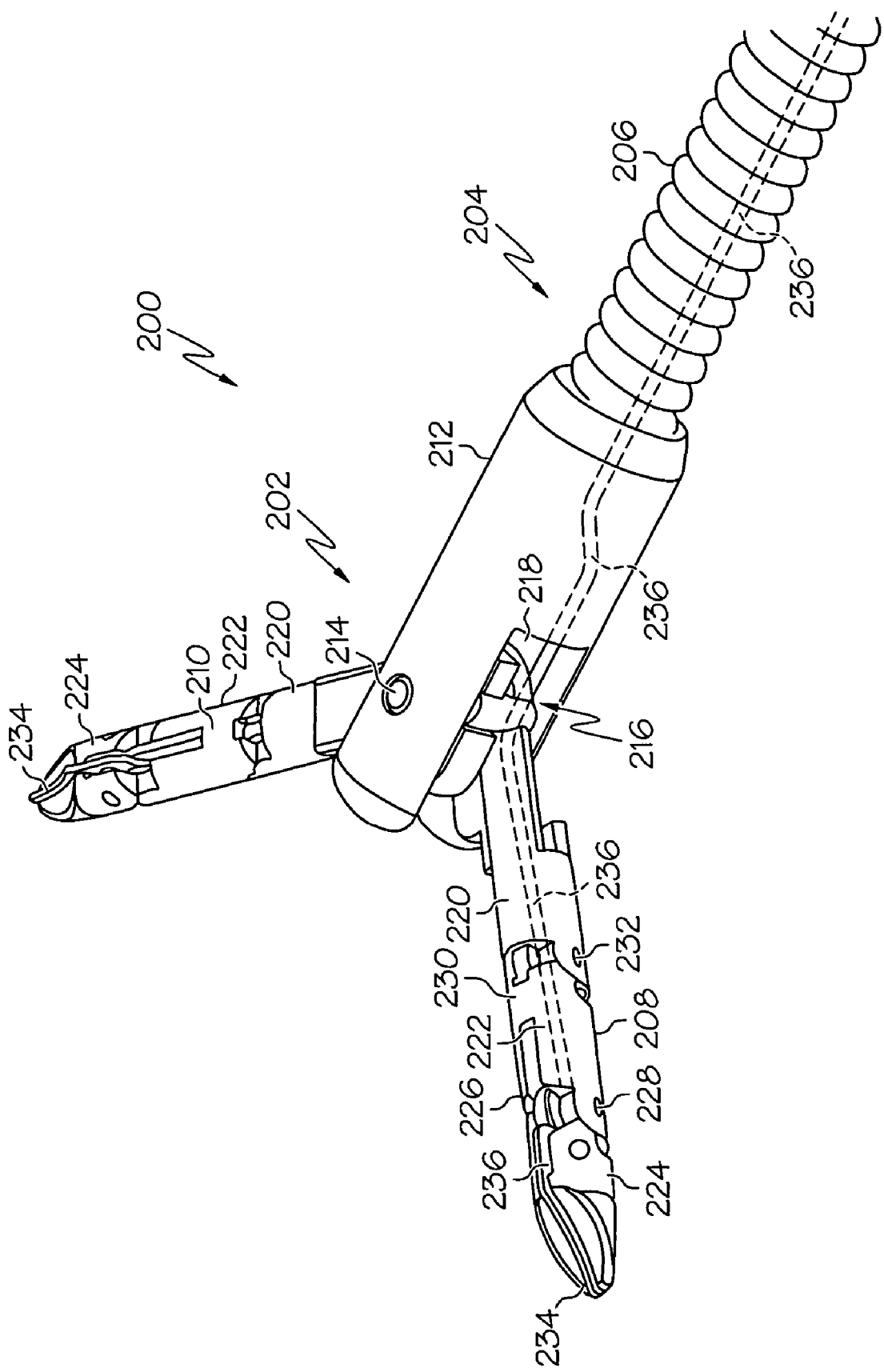
FIG. 5 is a perspective view of an alternative aspect of the disclosed apparatus for performing an EMR procedure.
Figure 6:
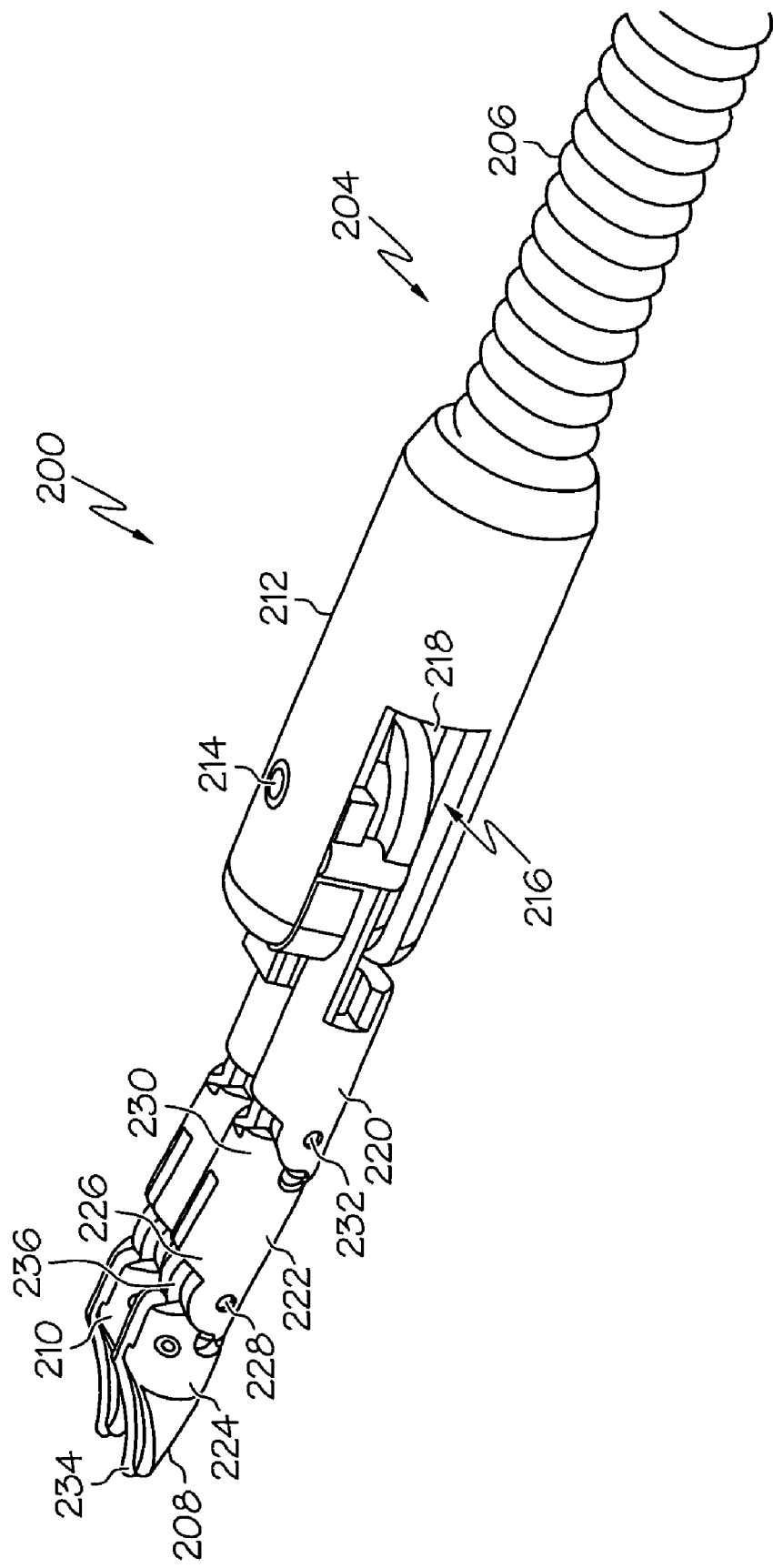
FIG. 6 is a perspective view of the apparatus of FIG. 5 in a second configuration.
Figure 7:
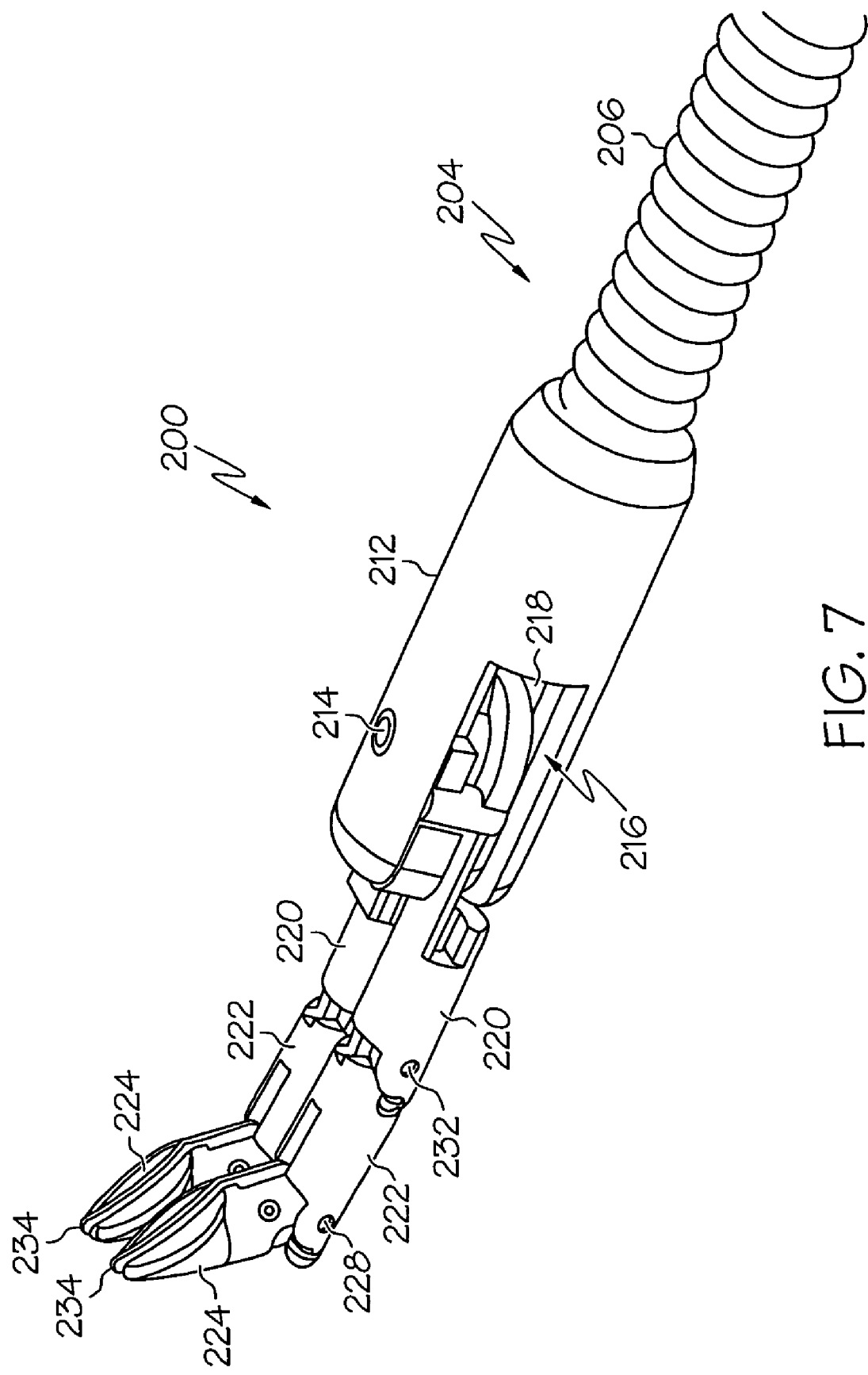
FIG. 7 is a perspective view of the apparatus of FIG. 6, wherein the cutting elements are in a partially deployed position.
Figure 8:
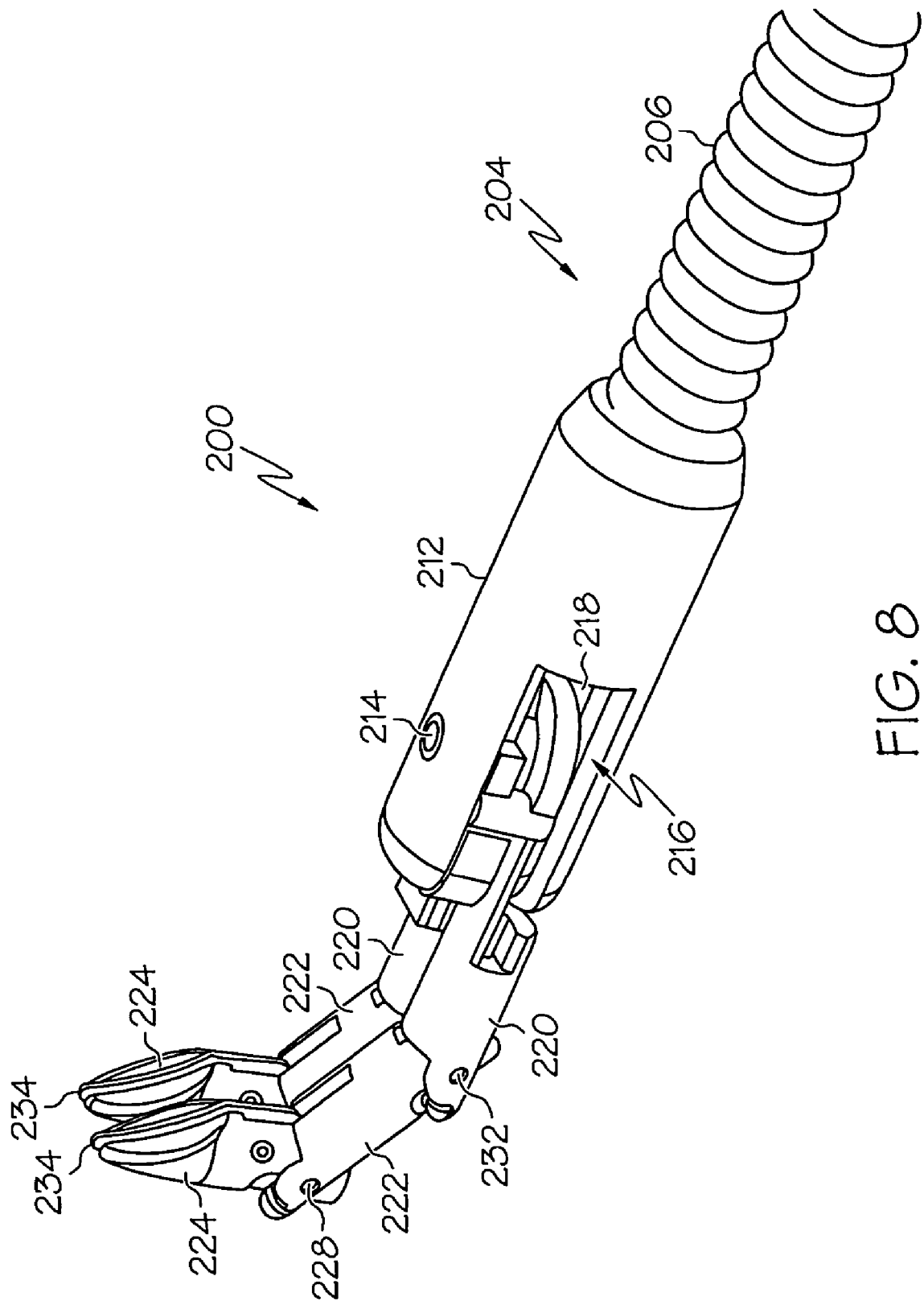
FIG. 8 is a perspective view of the apparatus of FIG. 6, wherein the cutting elements are in a fully deployed position.
Figure 9:
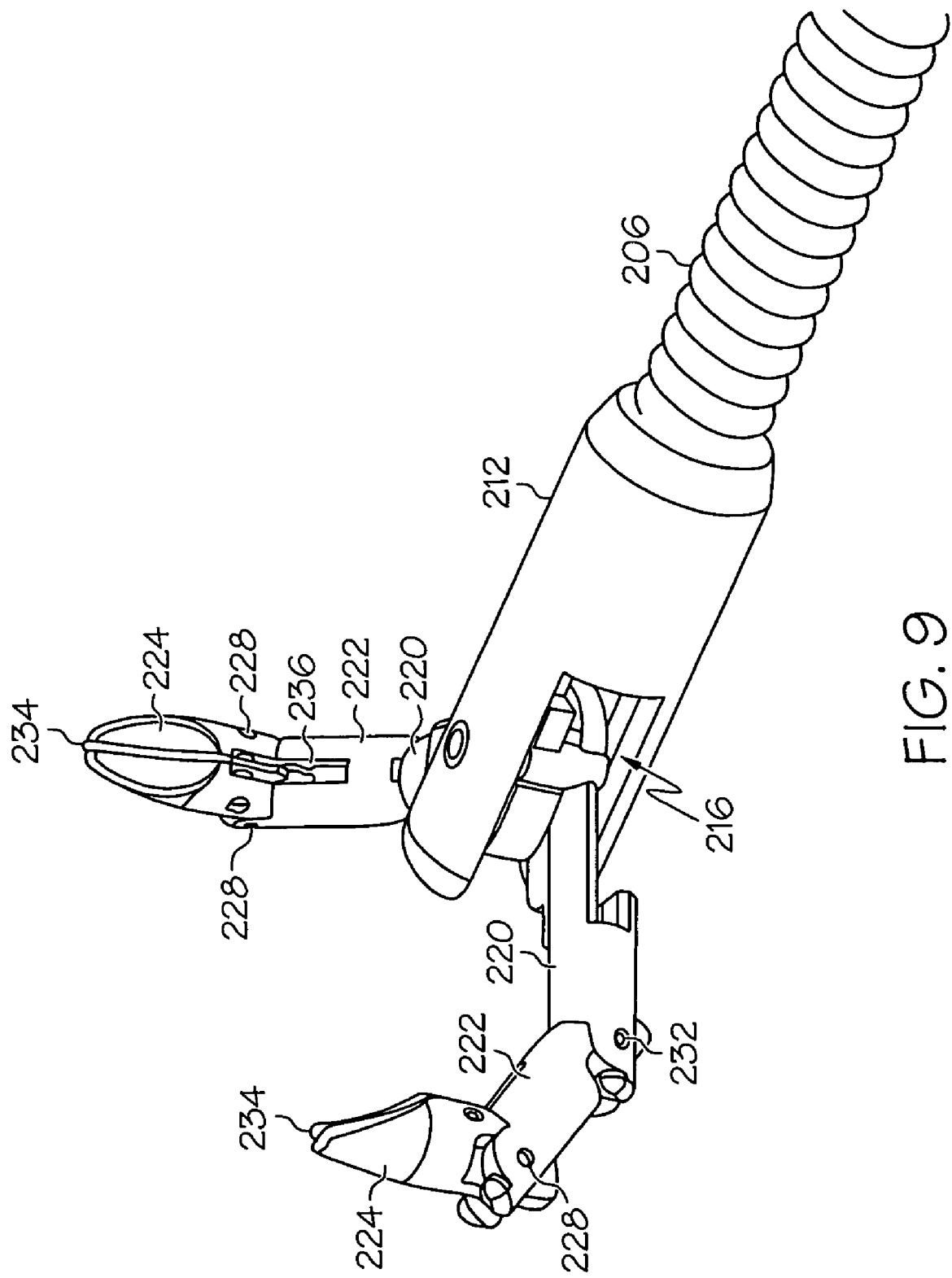
FIG. 9 is a perspective view of the apparatus of FIG. 8 in the second configuration.

The assembly 202 may include first and second moveable arms 208, 210 pivotally connected to a head 212 at a pivot point 214. A linkage assembly 216 and associated actuation cable 218 may be connected to the arms 208, 210 to allow a user to move the first arm relative to the second arm by manipulating the actuation cable 218 (e.g., by way of the user controls). For example, the arms 208, 210 may move in a scissor-like fashion through a dissection plane, as shown in FIGS. 5 and 6.

Each arm 208, 210 may be comprised of three pivotally connected links: a proximal link 220, a middle link 222 and a distal or tip link 224. The proximal link 220 of arm 208 may be pivotally connected to the proximal link 220 of arm 210 at the pivot point 214. The middle link 222 of each arm 208, 210 may include a distal portion 226 pivotally connected to the tip link 224 at pivot point 228 and a proximal portion 230 pivotally connected to the proximal link 220 at pivot point 232.

The tip link 224 of each arm 208, 210 may include a cutting element 234 thereon. The cutting element 234 may be a monopolar knife, an electrocautery knife or other electrically activated cutting device. Alternatively the cutting element 234 may be a mechanical cutting device such as a scalpel or the like. Optionally, the cutting element 234 may be retractable within an associated arm 208, 210 such that the cutting elements 234 may be deployed only when needed.

An actuating wire or cable 236 may be connected to the tip link 224 and may extend through the middle and proximal links 222, 220, through the head 212 and shaft 206 and may be presented for manipulation at the proximal end of the shaft 206 (e.g., at the user controls). Therefore, a force (e.g., pulling, pushing, twisting or the like) may be applied to the cable 236 to urge the links 126 of the arms 208, 210 from the position shown in FIG. 6, to the partially deployed position shown in FIG. 7 and, finally, to the fully deployed position shown in FIG. 8 (or various positions therebetween).

Thus, when the arms 208, 210 are in the fully deployed position, the cutting elements 234 may be positioned generally perpendicular or at least partially transverse with respect to the plane of movement (i.e., the dissection plane) of the arms 208, 210.

In one aspect, the actuation cable 236 may be electrically conductive and may electrically connect the cutting element 234 to a power source (not shown) (e.g., a source of monopolar electrical energy), thereby serving as an actuating element for deploying the cutting element 234 and as a conductor for supplying electrical energy to the cutting element 234.

At this point, those skilled in the art will appreciate that the EMR devices disclosed herein allow a user to control the relative movement of two or more arms in an opening-and-closing-type action generally through a blunt dissection plane and deploy cutting elements in a direction that is generally perpendicular or at least partially transverse to the blunt dissection plane. Furthermore, those skilled in the art will appreciate that various deployable cutting element assemblies may be used with the devices described herein.

Referring to FIGS. 10A and 10B, a first alternative aspect of a deployable cutting element assembly, generally designated 300, may include a wire 302 extending through an internal channel 304 of an associated arm 306 (e.g., arm 110) of the device (e.g., device 100). A distal portion 308 of the wire 302 may exit the internal channel 304 by way of an opening 310 in the arm 306. The proximal portion 312 of the wire 302 may extend through the arm 306 and the associated device such that it may be externalized and/or manipulated by a user (e.g., by way of user controls (not shown)) and connected to a source of monopolar electrical energy (not shown).

The distal most tip 314 of the wire 302 may be fixedly connected to the arm 306 such that, when the wire 302 is urged in the direction shown by arrow D, the distal portion 308 of the wire 302 may extend radially with respect to the associated arm 306 and may form a cutting tip 316, as shown in FIG. 10B.

Thus, the cutting element may be deployed by urging the wire 302 in the direction of arrow D and withdrawn by urging the wire 302 in the direction shown by arrow E. The cutting tip 316 may serve as a monopolar knife when electrical energy is supplied to the wire 302.

Referring to FIGS. 11A and 11B, a second alternative aspect of a deployable cutting element assembly, generally designated 400, may include a first link 402, a second, distal link 404, a third link 406 and a cutting element 408. The cutting element 408 may be fixedly connected to the distal link 404.

The cutting element 408 may be an electrode of an electrically actuated cutting device and may be electrically connected to an electrical power supply (not shown). Alternatively, the cutting element 408 may be a mechanical cutting device, such as a scalpel or the like.

The links 402, 404, 406 may be arranged such that movement of the first link 402 relative to the third link 406 causes the cutting element to move from the un-deployed position shown in FIG. 11A to the deployed position shown in FIG. 11B. In one aspect, the first link 402 may be connected to the second link 404 by a first hinge 410 and the third link 406 may be connected to the second link 404 by a second hinge 412. First and/or second hinges 410, 412 may be living hinges, pivot points or the like.

Thus, movement of the third link 406 relative to the first link 402 in the direction shown by arrow F may urge the cutting element 408 to the deployed position.

Referring to FIGS. 12A and 12B, a third alternative aspect of a deployable cutting element assembly, generally designated 500, may include a first electrically insulating sheath 502, a second electrically insulating sheath 504, two flexible coils 506, 508 and a cutting element 510. The first flexible coil 506 may extend through the first sheath 502 and the second flexible coil 508 may extend through the second sheath 504. The distal portions 512 of the flexible coils 506, 508 may be connected to each other to form a tip 514 and the cutting element 510 may be fixedly connected to the tip 514.

The cutting element 510 may be an electrode of an electrically actuated cutting device and may be electrically connected to an electrical power supply (not shown). For example, at least one of the flexible coils 506, 508 may serve as a conductor to electrically couple the cutting element 510 to the electrical power supply. Alternatively, the cutting element 408 may be a mechanical cutting device, such as a scalpel or the like.

Accordingly, the cutting element 510 may be deployed from the first configuration shown in FIG. 12A to the second configuration shown in FIG. 12B by urging the first coil 506 in the direction shown by arrow G and/or the second coil 508 in the direction shown by arrow H.

At this point, those skilled in the art will appreciate that assemblies 300, 400 and/or 500 may serve as the arms of the EMR devices disclosed herein (e.g., arms 110, 112 or arms 208, 210). Alternatively, the assemblies 300, 400 and/or 500 may be separate from and/or may be disposed within the arms of the EMR devices disclosed herein.

Referring to FIGS. 13-21, the apparatus and methods described herein may be employed to resect a lesion 600 or other suspect tissue or growth from the intestinal wall 602 of a patient during an endoscopic procedure. However, those skilled in the art will appreciate that the apparatus and methods described herein may be used to perform various other medical procedures, including removing suspect tissue from the esophageal wall or other tissue or organs of the body.

The intestinal wall 602 typically is comprised of four layers: the mucosa 604, the submucosa 606, the muscularis 608 and a thin layer of serosa 610. Successful treatment typically requires the resection of the lesion 600 as well the adjacent portions of the mucosa 604 and submucosa 606 without penetrating the muscularis 608. Therefore, the apparatus and methods described herein allow a physician to separate the mucosa 604 and submucosa 606 adjacent to the lesion 600 (i.e., the target tissue 612) and resect the target tissue 612 without penetrating the muscularis 608.

Figure 13:
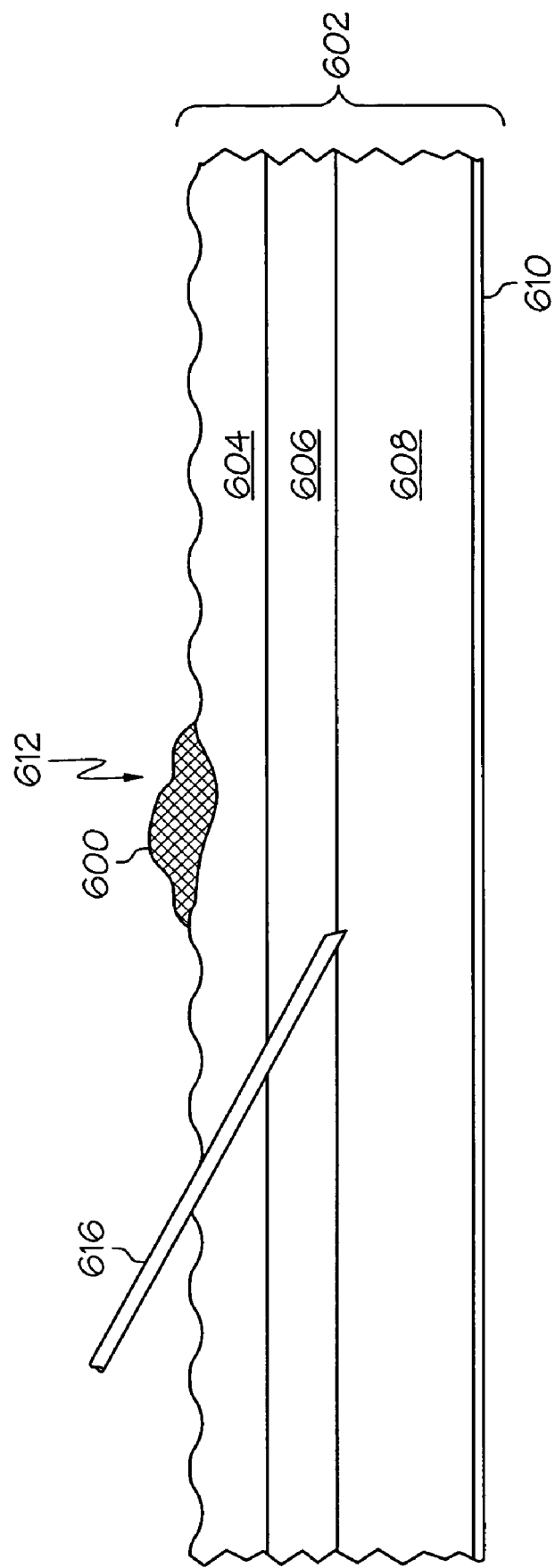
FIG. 13 is cross-sectional view of a gastrointestinal wall of a human patient.
Figure 14:
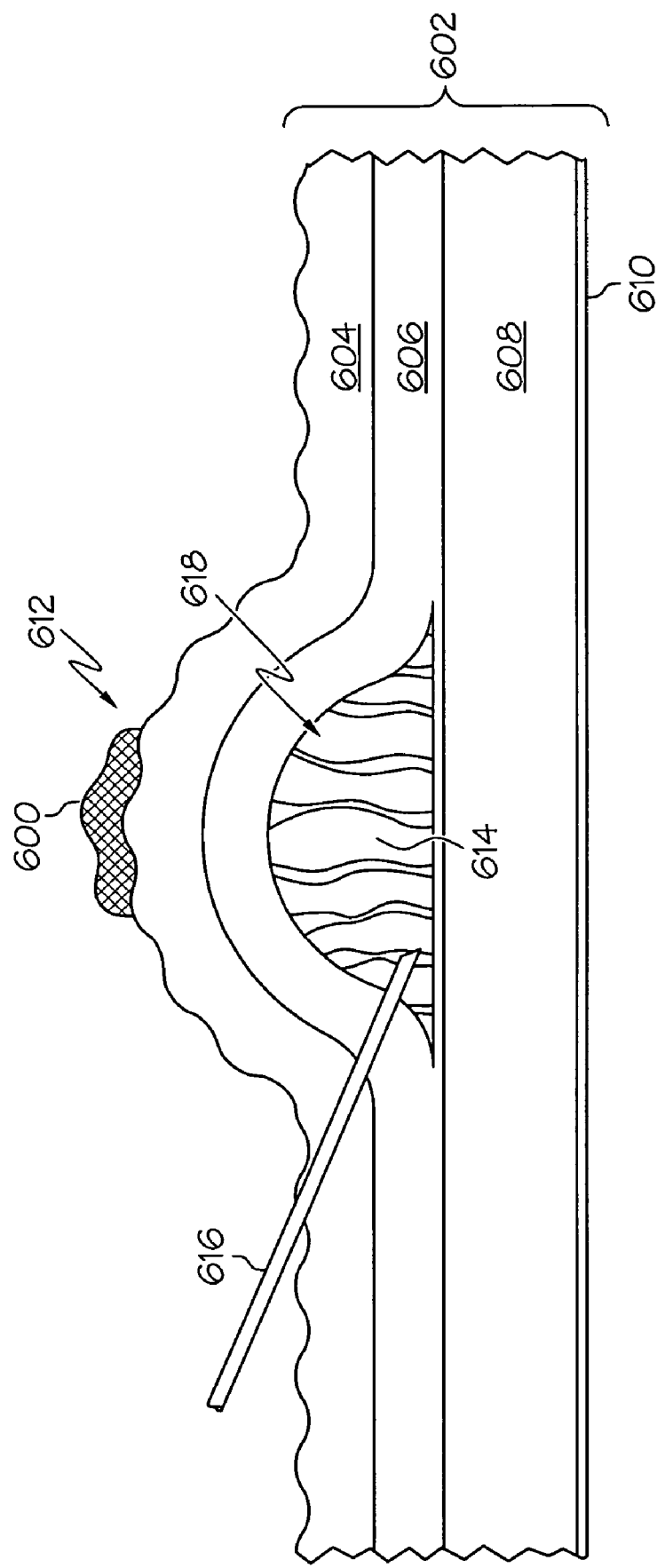
FIG. 14 is a cross-sectional view of the gastrointestinal wall of FIG. 13 according to an aspect of the disclosed method for performing an EMR procedure.

Referring to FIGS. 13 and 14, a physician optionally may facilitate or initiate the separation of the mucosa 604 and submucosa 606 from the muscularis 608 by injecting a fluid 614 into the submucosa 606 with an injection needle 616 or the like. The fluid 614 may be a liquid, such as a sterile saline solution, or a gas, such as carbon dioxide gas. As shown in FIG. 14, the fluid 614 may form a cushion 618 in the submucosa 606 and may elevate the target tissue 612, thereby facilitating the insertion of an EMR device.

In one aspect, the injection needle 616 may be mounted on or otherwise connected to an arm of the EMR device. In another aspect, the injection needle 616 may be retractable within an arm of the EMR device.

Figure 15:
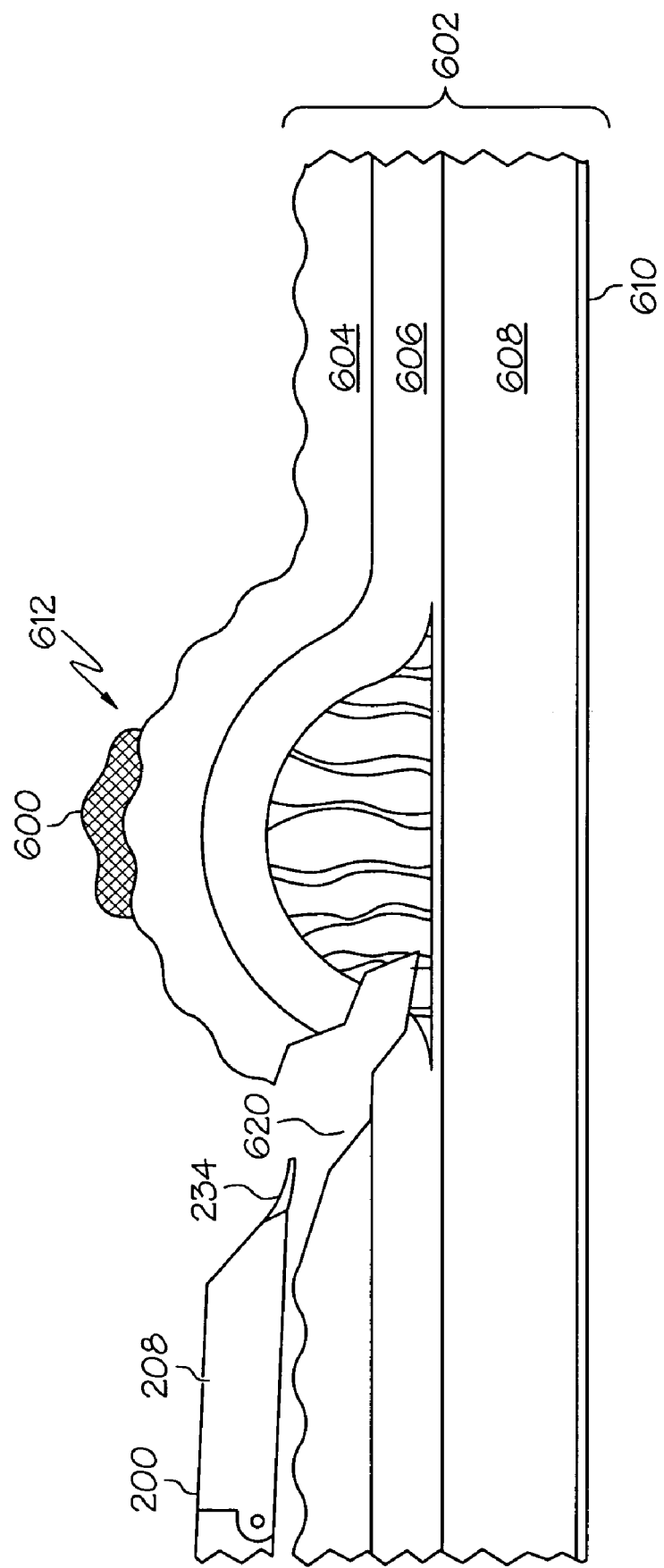
FIG. 15 is a cross-sectional view of the gastrointestinal wall of FIG. 14 according to an aspect of the disclosed method for performing an EMR procedure.
Figure 16:
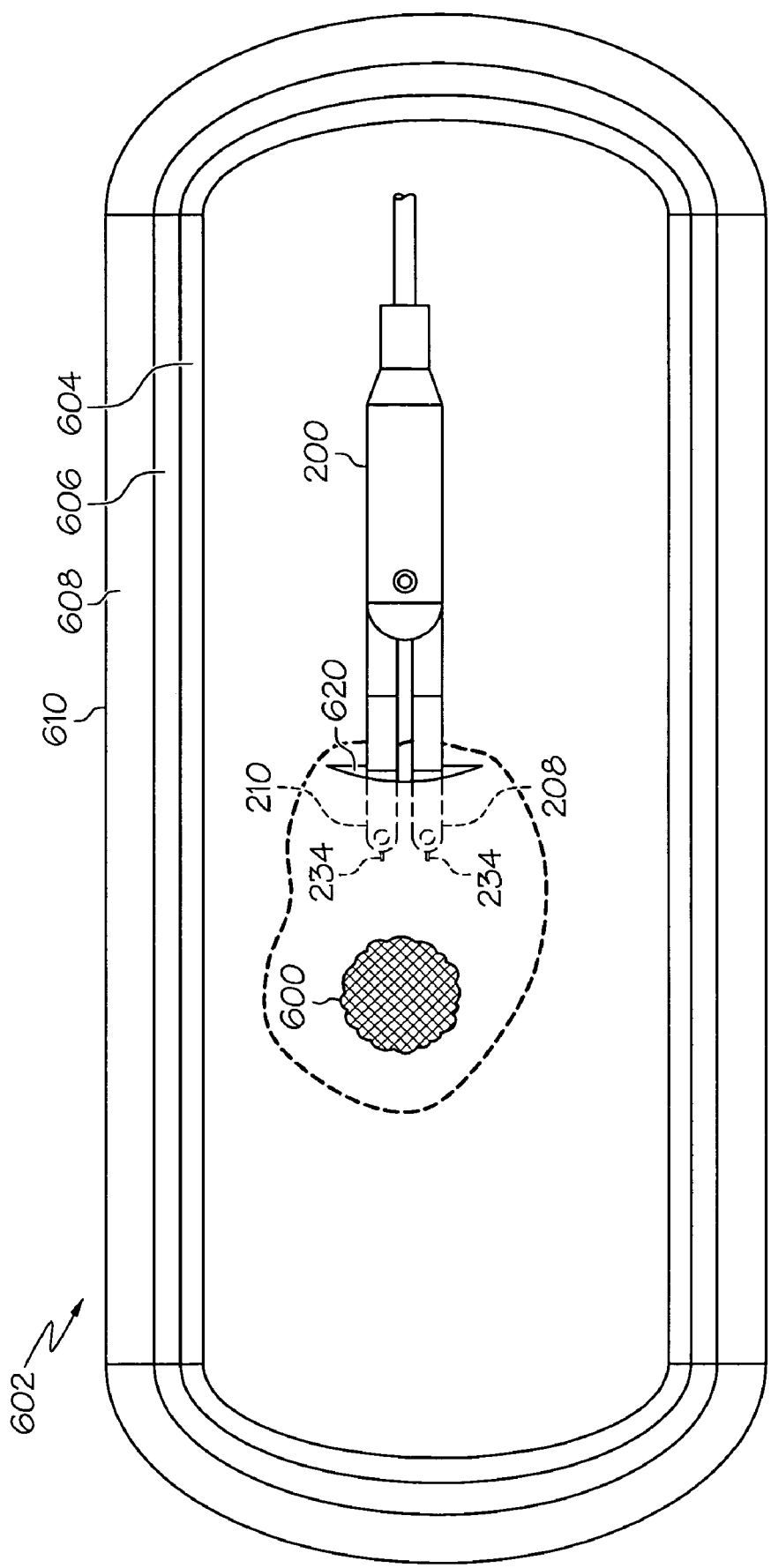
FIG. 16 is a top plan view, partially in section, of the gastrointestinal wall of FIG. 15, wherein the apparatus of FIG. 6 is inserted through the incision shown in FIG. 15 according to an aspect of the disclosed method for performing an EMR procedure.

Referring to FIGS. 15 and 16, a physician may form an initial incision 620 through the mucosa 604 and submucosa 606 into the target tissue 612, thereby providing access to the region between the submucosa 606 and the muscularis 608 beneath the target tissue 612. In one aspect, the incision 620 may be made with a knife or scalpel using any available surgical tools or techniques. In another aspect, the incision 620 may be made using an EMR device disclosed herein.

Referring again to FIGS. 15 and 16, and referring to device 200 as an example only, the device 200 may be configured in the un-deployed position (see FIG. 6) and the cutting elements 234 may be actuated with, for example, monopolar electrical energy. The incision 620 may be formed by applying the actuated cutting elements 234 to the tissue such that the cutting elements 234 penetrate the mucosa 604 and submucosa 606 and provide access to the region between the submucosa 606 and the muscularis 608. The size of the incision 620 may be increased by displacing the arms 208, 210 of the device 200 while the cutting elements 234 are actuated.

At this point, those skilled in the art will appreciate that the initial incision 620 may be formed using the cutting elements described above (i.e., the cutting elements used to resect suspect tissue). However, those skilled in the art will also appreciate that the EMR devices disclosed herein may have a separate and/or independent cutting system for creating the initial incision 620.

Figure 17:
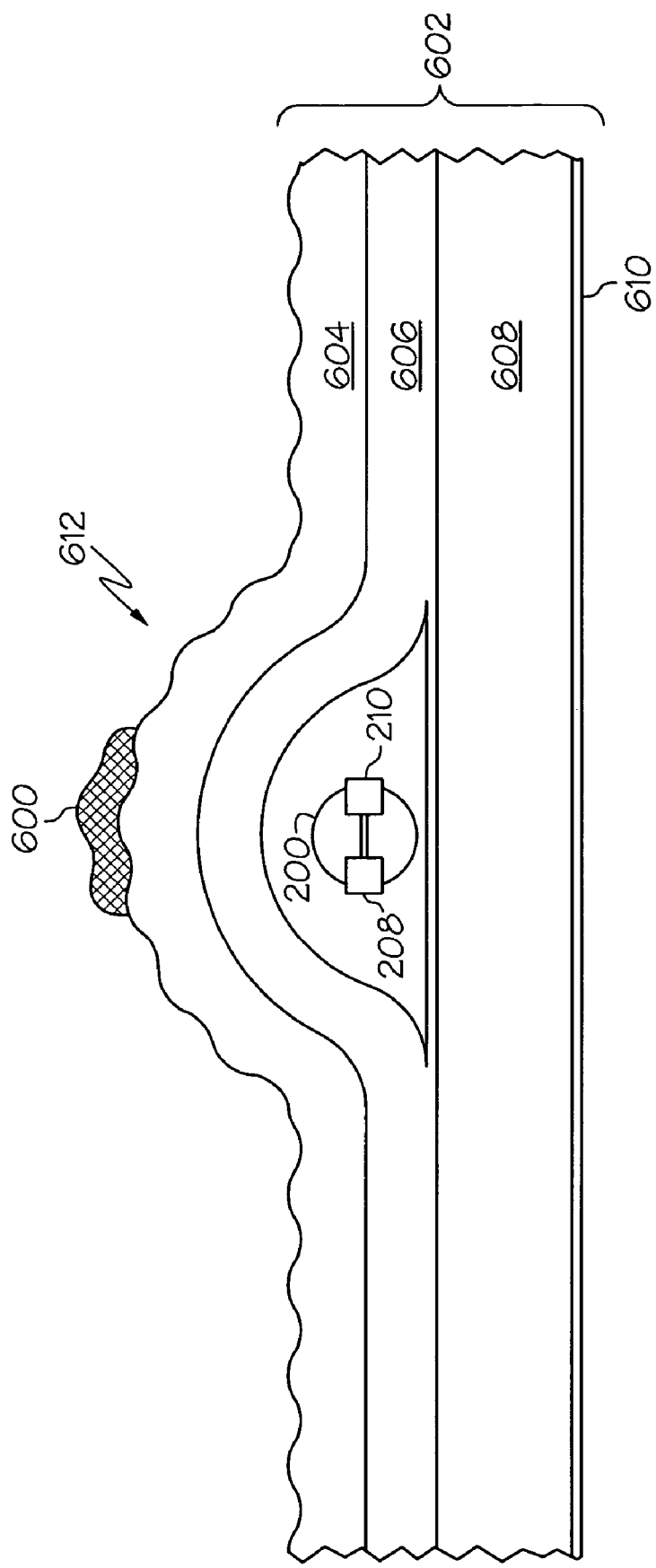
FIGS. 17 and 18 are cross-sectional views of the gastrointestinal wall of FIG. 15, wherein the apparatus of FIG. 5 is performing a blunt dissection procedure according to an aspect of the disclosed method for performing an EMR procedure.
Figure 18:
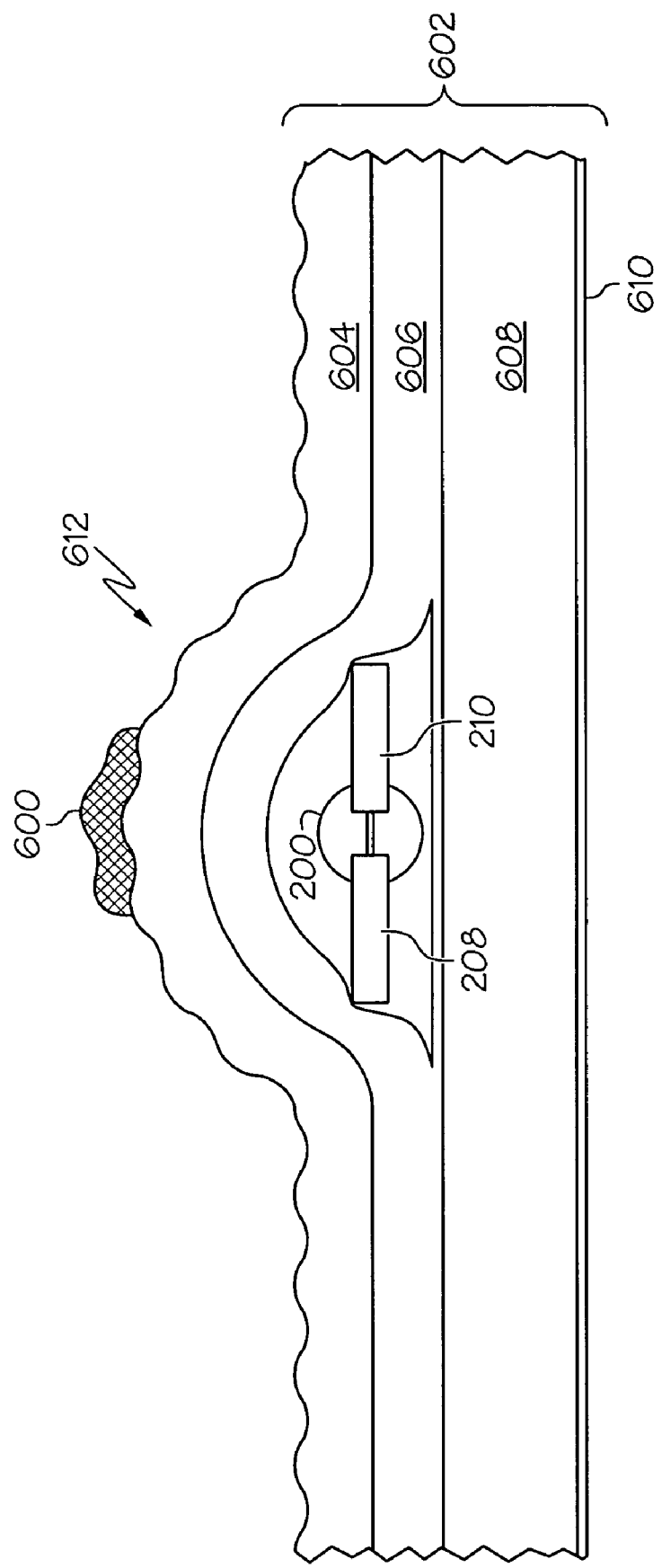

The device 200 may be inserted through the initial incision 620 and positioned between the submucosa 606 and the muscularis 608. As shown in FIGS. 17 and 18, using the scissor-like action of the arms 208, 210 described herein, the device 200 may advanced beneath the target tissue 612 to separate or bluntly dissect the submucosa 606 from the muscularis 608 and, if necessary, disconnect any connective tissue therebetween.

Figure 19:
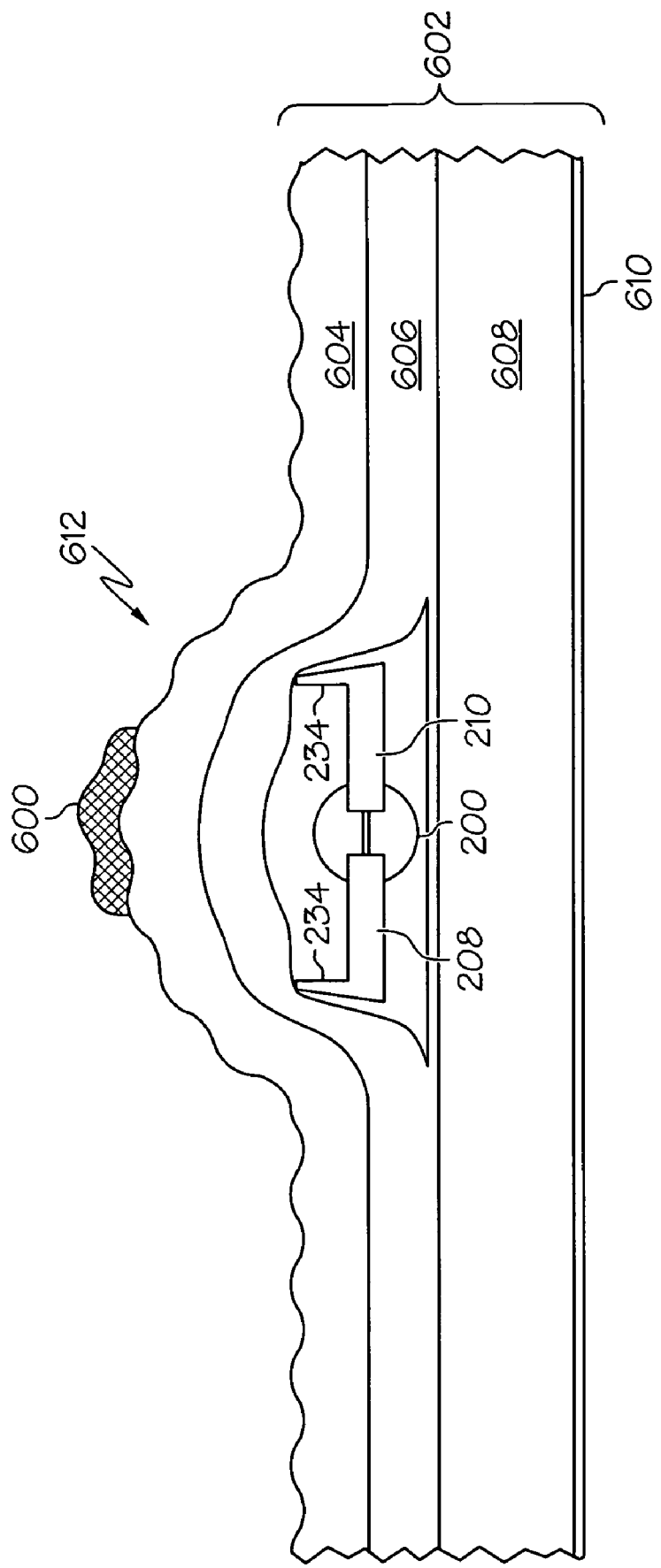
FIG. 19 is a cross-sectional view of the gastrointestinal wall of FIG. 18 after deployment of cutting elements according to an aspect of the disclosed method for performing an EMR procedure.

Once the target tissue 612 has been separated from the muscularis 608, the cutting elements 234 may be configured to the deployed position such that the cutting elements 234 are at least partially transverse with respect to the blunt dissection plane, as shown in FIG. 19. In one aspect, the cutting elements 234 may be deployed such that they cut the submucosa 606 and mucosa 604 above the device 200 (i.e., away from the muscularis 608). In another aspect, the cutting elements 234 may be deployed such that they are directed towards the center of the lumen formed by the intestinal wall 602.

Figure 20:
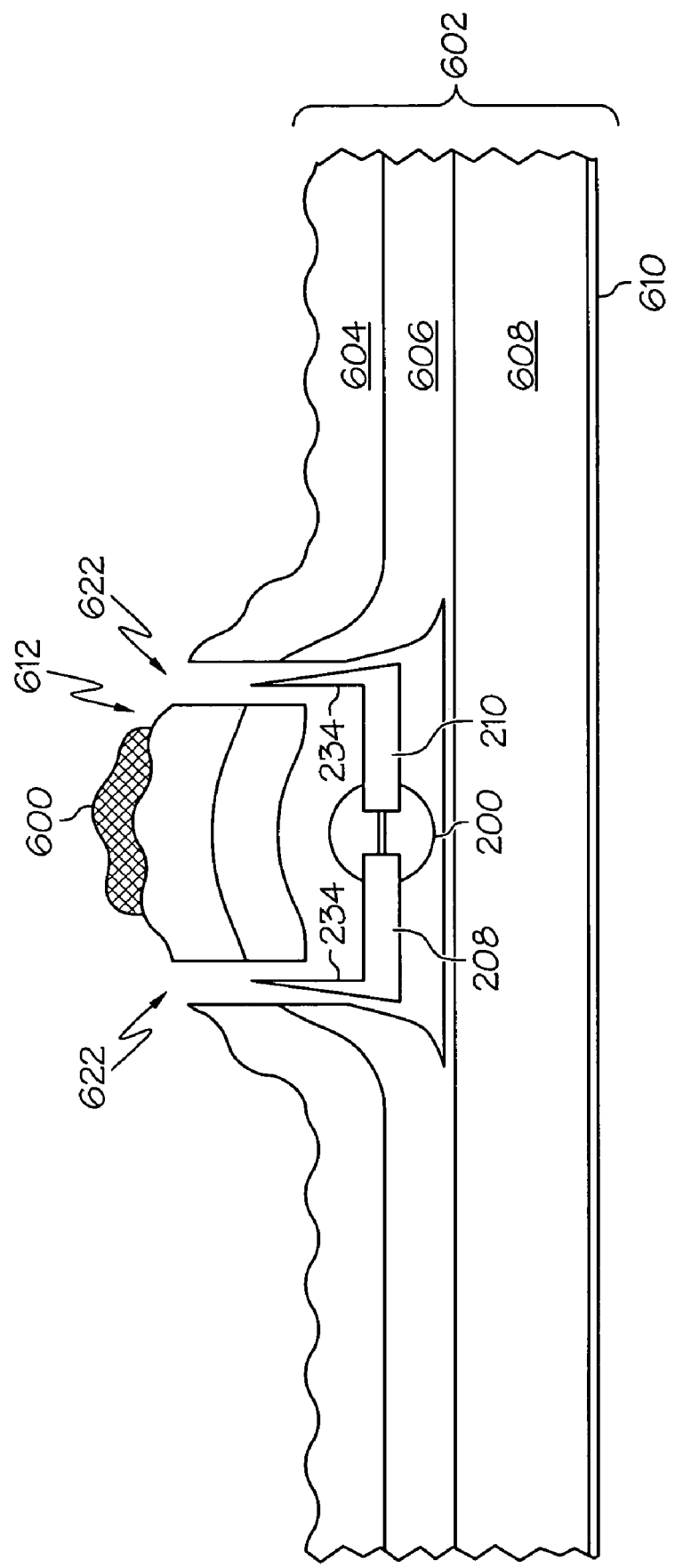
FIG. 20 a cross-sectional view of the gastrointestinal wall of FIG. 19 depicting a resection of suspect tissue according to an aspect of the disclosed method for performing an EMR procedure.
Figure 21:
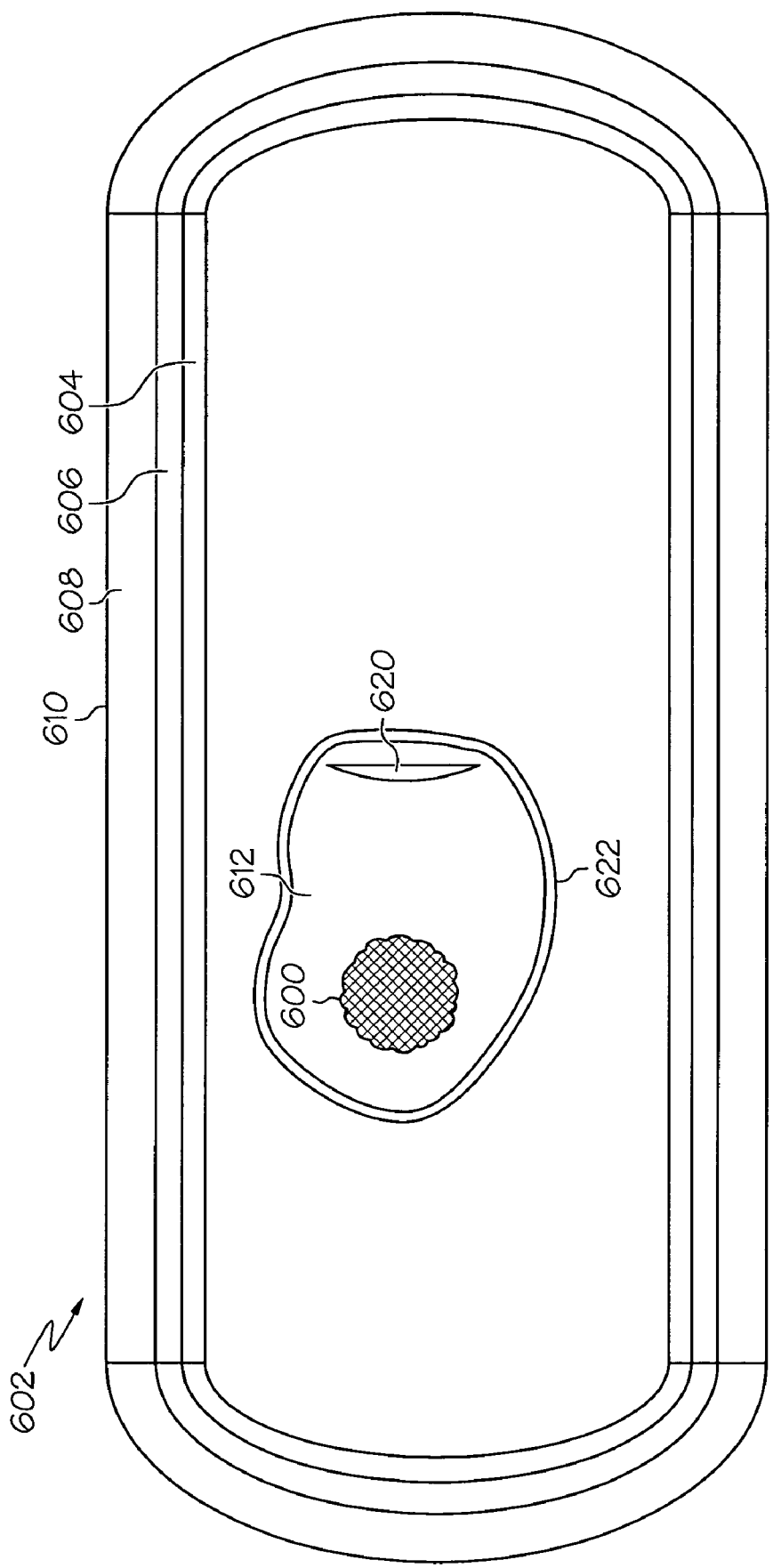
FIG. 21 is top plan view, partially in section, of the gastrointestinal wall of FIG. 20.

Referring to FIGS. 20 and 21, once the cutting elements 234 are deployed and actuated (e.g., with monopolar electrical energy), the target tissue 612 may be resected by advancing and/or retracting the device 200 through the region between the muscularis 608 and the submucosa 606, while opening and closing the arms 208, 210 in the scissor-like action describe herein. The resulting cut 622 may free the target tissue 612 from the intestinal wall 602 such that it may be removed from the gastrointestinal tract using, for example, a snare, graspers or the like.

Thus, the apparatus and methods disclosed herein allow a physician to resect suspect tissue from the intestinal wall 602 by bluntly dissecting the submucosal layer 606 from the muscularis 608 adjacent to the target tissue 612 and, working with cutting elements (e.g., cutting elements 234) that are directed away from the plane of the muscularis 608, cutting around the target tissue 612.

Although various aspects of the disclosed apparatus and methods have been shown and described, modifications may occur to those skilled in the art upon reading the specification. The present application includes such modifications and is limited only by the scope of the claims.

What is claimed is:

1. A method for resecting tissue from an organ of a patient, said organ being comprised of at least a first layer, a second layer and a third layer, said method comprising the steps of:
   providing an EMR device with access to said organ, said EMR device including at least one deployable cutting element disposed on at least one moveable arm, said moveable arm defining an axis, said cutting element being deployable from a first configuration, wherein said cutting element is generally aligned with said axis, to a second configuration, wherein said cutting element is generally transverse to said axis;
   identifying a target tissue area for resection;
   forming an incision through said first and second layers without penetrating said third layer;
   positioning said EMR device through said incision such that said device is positioned between said first and said third layers;
   advancing said moveable arm between said first and said third layers;
   deploying said cutting element from said first configuration to said second configuration such that said cutting element is advanced in the direction of said first layer and away from said third layer; and
   while said EMR device is positioned between said first and said third layers, cutting through said first layer.

2. The method of claim 1 wherein said incision forming step includes forming said incision with said cutting element of said EMR device.

3. The method of claim 1 wherein said cutting element is a monopolar knife.

4. The method of claim 1 further comprising the step of injecting a fluid between said first and said third layers in said target tissue area.

5. The method of claim 4 wherein said fluid is injected in said second layer.

6. The method of claim 4 wherein said fluid is at least one of a liquid and a gas.

7. The method of claim 4 wherein said fluid is injected with an injection needle connected to said EMR device.

8. The method of claim 4 wherein said injecting step is performed prior to said forming an incision step.

9. The method of claim 1 wherein said cutting step includes supplying electrical energy to said cutting element to aid in said cutting step.

10. The method of claim 9 wherein said electrical energy is monopolar electrical energy.

11. The method of claim 1 wherein said cutting step includes cutting around said target tissue area.

12. The method of claim 1 wherein said organ is a human colon, said first layer is a mucosal layer of said human colon, said second layer is a submucosal layer of said human colon and said third layer is a muscularis layer of said human colon.

13. The method of claim 1 wherein said providing step includes passing said EMR device through a natural orifice of a human body.

14. A method for resecting tissue from an organ of a patient, said organ being comprised of at least a first layer, a second layer and a third layer, said method comprising the steps of:
   providing an EMR device with access to said organ, said EMR device including a first moveable arm including a first deployable cutting element and a second moveable arm including a second deployable cutting element, wherein said first moveable arm defines a first axis and said first deployable cutting element is deployable from a first configuration, wherein said first cutting element is generally aligned with said first axis, to a second configuration, wherein said first cutting element is generally transverse to said first axis, and wherein said second moveable arm defines a second axis and said second deployable cutting element is deployable from a third configuration, wherein said second cutting element is generally aligned with said second axis, to a fourth configuration, wherein said second cutting element is generally transverse to said second axis;

identifying a target tissue area for resection;

injecting a fluid between said first layer and said third layer in said target tissue area;

forming an incision through said first and second layers without penetrating said third layer;

positioning said EMR device through said incision such that said device is positioned between said first and said third layers;

separating said first layer from said third layer by advancing said first and second moveable arms between said first layer and third layer;

deploying said first cutting element from said first configuration to said second configuration and said second cutting element from said third configuration to said fourth configuration such that said first and second cutting elements are advanced in a direction of said first layer and away from said third layer; and while said EMR device is positioned between said first and said third layers, cutting through said first layer to resect said target tissue area.

15. A method for resecting tissue from an organ of a patient, said organ being comprised of at least a first layer and a second layer, said method comprising the steps of:

positioning an EMR device between said first layer and said second layer, said EMR device including at least one deployable cutting element disposed on at least one moveable arm, said moveable arm defining an axis, said cutting element being deployable from a first configuration, wherein said cutting element is generally aligned with said axis, to a second configuration, wherein said cutting element is generally transverse to said axis;

advancing said moveable arm between said first layer and said second layer to separate said first layer from said second layer;

deploying said cutting element from said first configuration to said second configuration such that said cutting element is advanced in a direction of said first layer and generally away from said second layer; and while said cutting element is advanced in said direction of said first layer, cutting through said first layer.

* * * * *